(12) United States Patent
Mizutani et al.

(10) Patent No.: US 6,548,158 B2
(45) Date of Patent: Apr. 15, 2003

(54) ABSORBENT ARTICLE WITH PERFORATED TOP SHEET

(75) Inventors: Satoshi Mizutani, Kagawa (JP); Tatsuya Tamura, Kagawa (JP); Yuuki Noda, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 154 days.

(21) Appl. No.: 09/740,646

(22) Filed: Dec. 19, 2000

(65) Prior Publication Data

US 2001/0007066 A1 Jul. 5, 2001

(30) Foreign Application Priority Data

Dec. 22, 1999 (JP) ............................................. 11-364237

(51) Int. Cl.$^7$ ............................... B32B 5/14; B32B 5/16
(52) U.S. Cl. ..................... 428/323; 442/394; 428/137; 428/138; 604/385.1
(58) Field of Search .......................... 442/394; 428/323, 428/137, 138; 604/385.1

(56) References Cited

U.S. PATENT DOCUMENTS 4,690,679 A  *  9/1987  Mattingly, III et al. ..... 604/383

FOREIGN PATENT DOCUMENTS

| JP | 05-200065 | 8/1993 |
|----|-----------|--------|
| JP | 9-505223  | 5/1997 |

* cited by examiner

Primary Examiner—Terrel Morris
Assistant Examiner—John J. Guarriello
(74) Attorney, Agent, or Firm—Darby & Darby

(57) ABSTRACT

Provided is an absorbent article including an absorbent layer and a top sheet having a number of perforations and disposed on a body facing surface of the absorbent layer. The top sheet is made of a multi-layered resin film having at least two resin layers composing of an outer resin layer exposed outside the body facing surface and at least one inner resin layer disposed nearer to the absorbent layer than the outer resin layer thereto. At least, the outer resin layer contains a particulate material having a mean particle size of from 2 $\mu$m to 20 $\mu$m, and the inner resin layer has the resin density smaller than that of the outer resin layer.

12 Claims, 2 Drawing Sheets

ABSORBENT ARTICLE WITH PERFORATED TOP SHEET

BACKGROUND OF THE INVENTION

1. Field of the Invention

The present invention relates generally to an absorbent article for sanitary napkins, pantiliners, incontinence pads, etc. More precisely, the invention relates to such an absorbent article of which the top sheet has a good feel.

2. Description of the Related Art

Absorbent articles are much used these days for sanitary napkins, pantiliners, incontinence pads, disposable diapers and the like for absorbing excretions. Such absorbent articles generally comprise a liquid pervious top sheet to face a wearer (serving as a body facing face), a liquid impervious back sheet, and a liquid absorbing layer sandwiched between the top sheet and the back sheet. The top sheet is directly contacted with the skin of a wearer, so that it is desirable to have a good feel. In addition, since the top sheet directly receives excretions, it is preferable that liquid excretions hardly stay therein so that the top sheet itself does not become stuffy and sticky.

For example, Japanese Unexamined Patent Publication (Kokai) No. Heisei 5-200065 discloses a surface member for absorbent articles, which has a fine embossed pattern on its surface. As having a fine embossed pattern, the surface member disclosed does not have a plastic-like feel, and is not sticky. In this case, this is not sticky in dry, but when wetted, it shall have power of resistance to liquid flow thereon owing to its embossed pattern, and tends to keep the liquid in the recesses on its surface.

International Unexamined Patent Publication (Kohyo) No. Heisei 9-505223 discloses a liquid pervious, porous plastic web containing a particulate material. The web is formed into a top sheet for absorbent articles, and this has a little plastic-like feel. However, the web containing the particulate material is rigid, and the top sheet made of it is poorly flexible.

SUMMARY OF THE INVENTION

The present invention has an object to provide an absorbent article of which the top sheet is not sticky even in wet and is highly flexible, thereby all the time having a good feel.

Another object of the invention is to provide an absorbent article of which the top sheet has shape retaining perforations.

According to an aspect of the invention, the absorbent article of the invention may comprise an absorbent layer and a top sheet having a number of perforations and disposed on a body facing surface of the absorbent layer, wherein;

the top sheet is made of a multi-layered resin film having at least two resin layers composing of an outer resin layer exposed outside the body facing surface and at least one inner resin layer disposed nearer to the absorbent layer than the outer resin layer thereto, at least the outer resin layer containing particulate material having a mean particle size of from 2 $\mu$m to 20 $\mu$m, and the inner resin layer having the resin density smaller than that of the outer resin layer.

With the top sheet of the absorbent article of the invention, the outer resin layer to be kept in direct contact with the skin of a wearer does not have a plastic-like feel, and little liquid remains therein. In its use, therefore, the top sheet does not become stuffy and sticky. On the other hand, the inner resin layer of the top sheet ensures the flexibility of the top sheet. In addition, the shape retaining ability of the perforations formed through the top sheet is good. Therefore, even if the perforations are deformed while the absorbent article is used, they can be readily restored to their original condition.

The top sheet of the absorbent article of the invention may be made of a two-layered resin film composed of an outer resin layer and an inner resin layer; or may be made of a multi-layered resin film having a third resin layer in addition to the outer and inner resin layers. For the latter, for example, the third resin layer may be sandwiched between the outer resin layer and the inner resin layer, or may be disposed inside the inner resin layer. The resin density of the third resin layer may be the same as that of the outer resin layer, or may fall between the resin density of the outer resin layer and that of the inner resin layer.

The inner resin layer is to ensure the flexibility of the top sheet comprising it. Therefore, it is desirable that the inner resin layer does not contain particulate material having a mean particle size of from 2 $\mu$m to 20 $\mu$m. However, the inner resin layer may contain such particulate material so far as the particulate material content of the inner resin layer is smaller than that of the outer resin layer.

In order to prevent too tight contact of the top sheet to the skin in practical use of the absorbent article, it is desirable that at least a part of the particulate material is exposed outside the outer resin layer.

For example, the resin density of the outer resin layer is at least 0.91 g/cm$^3$, and that of the inner resin layer is at most 0.90 g/cm$^3$.

Preferably, the outer resin layer contains from 30 to 60 parts by weight, relative to 100 parts by weight of the resin that forms the outer resin layer, of the particulate material.

Also preferably, the thickness of the outer resin layer is from 15 to 60% and the thickness of the inner resin layer is from 40 to 85%, relative to 100% of the thickness of the multi-layered resin film. This shall apply to both two-layered resin films and three-layered or more multi-layered resin films for the top sheet.

For example, the thickness of the multi-layered film for the top sheet falls between 20 and 35 $\mu$m.

Also for example, the top sheet of the absorbent article of the invention is a three-dimensionally perforated sheet in which the inner wall of each perforation protrudes from the inner surface of the top sheet toward the absorbent layer.

For example, the inner diameter of each perforation in the surface of the top sheet falls between 0.6 and 1.5 mm; the depth of each perforation from its top falls between 0.3 and 0.6 mm; and the distance between the neighboring perforations in the surface of the top sheet falls between 0.05 and 0.2 mm.

At least one resin layer of the multi-layered resin film may optionally contain fine particles having a particle size of from 0.01 $\mu$m to 0.5 $\mu$m, with the amount of the fine particles being not larger than 5 parts by weight relative to 100 parts by weight of the resin that forms the resin layer.

Containing such fine particles, the transparency of the top sheet may be lowered, and the blood or the like having been absorbed by the absorbent layer could be masked with them. In this case, the fine particles are, for example, titanium oxide particles.

The top sheet made of the multi-layered resin film may be partly bonded to the absorbent layer; or a water-impervious non-woven fabric may be bonded to the inner surface of the top sheet made of the multi-layered resin film to form a combined sheet, and the combined sheet of the top sheet and the non-woven fabric may be partly bonded to the absorbent layer.

DESCRIPTION OF THE PREFERRED EMBODIMENTS

Figure 1:
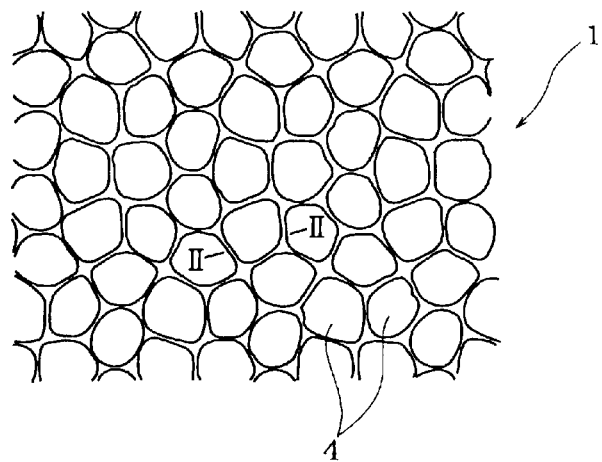
FIG. 1 is a partially enlarged plan view of one embodiment of an absorbent article of the invention, looking from its outer surface.
Figure 2:
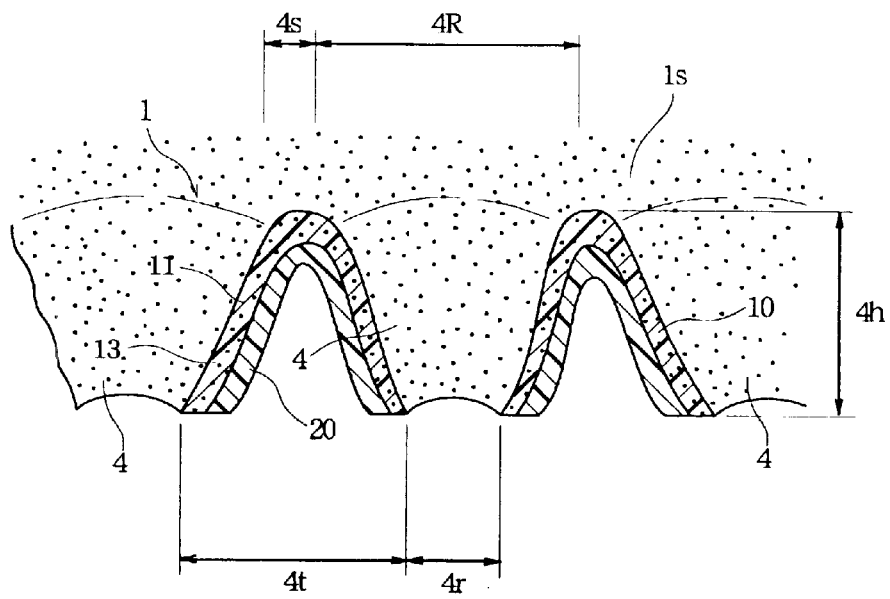
FIG. 2 is a partially enlarged cross-sectional view of the top sheet of FIG. 1, cut along the line II—II.
Figure 3:
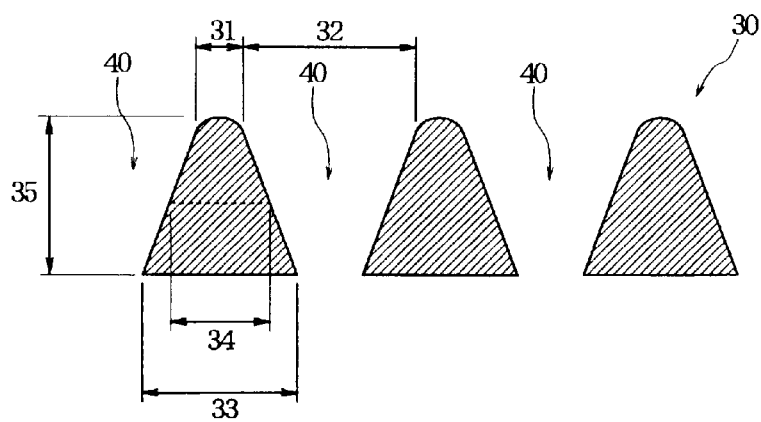
FIG. 3 is a partially enlarged cross-sectional view of a plastic sheet to be used for forming the top sheet.

FIG. 1 is a partially enlarged plan view of one embodiment of a top sheet for an absorbent article of the invention, looking from its outer surface; FIG. 2 is a partially enlarged cross-sectional view of the top sheet of FIG. 1, cut along the line II—II; FIG. 3 is a partially enlarged cross-sectional view of a plastic sheet to be used for forming the top sheet; and FIG. 4 is a cross-sectional view of one embodiment of the absorbent article of the invention, in which the top sheet of FIG. 1 is used.

The absorbent article of the invention is for sanitary napkins, pantiliners, incontinence pads, open-type or panty-type disposable diapers, and the like.

Figure 4:
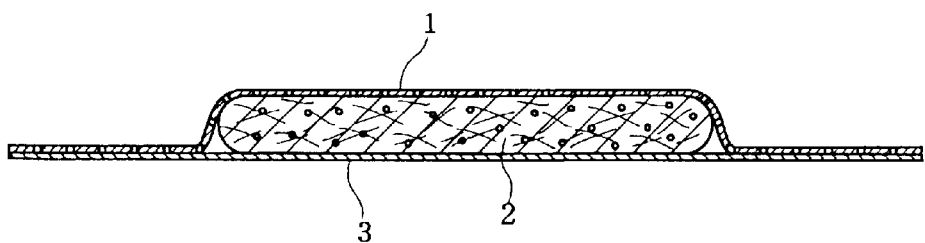
FIG. 4 is a cross-sectional view of one embodiment of the absorbent article of the invention, in which the top sheet of FIG. 1 is used.

The absorbent article of FIG. 4 comprises a top sheet 1 made of a multi-layered resin film (this is a two-layered resin film herein) and having a number of perforations formed therethrough; a liquid impervious back sheet 3; and an absorbent layer 2 sandwiched between the top sheet 1 and the back sheet 3. Excretions to be absorbed by the absorbent article fitted to a wearer are led through the number of perforations formed through the top sheet 1 to the absorbent layer 2.

The top sheet 1 of the embodiment illustrated in FIG. 2 is made of a two-layered laminate resin film composed of an outer resin layer 10 that shall face the skin of a wearer and an inner resin layer 20 that shall face the absorbent layer 2.

The outer resin layer 10 comprises essentially a thermoplastic resin 11 and contains a number of particles 13 of a particulate material. A part of the particles 13 are exposed outside a surface 1s of the outer resin layer 10 of the top sheet 1. With that, the filmy feel and the sticky feel of the surface of the top sheet 1 can be reduced.

The thermoplastic resin 11 for forming the outer resin layer 10 is selected from a group generally consisting of polyethylene, polypropylene, polyvinyl chloride, starch base resin, polyvinyl alcohol, polyurethane, polycaprolactone cellulose esters and blends thereof or the like, for example. Among those, preferred is LLDPE (linear low-density polyethylene). Preferably, the density of the thermoplastic resin 11 is at least 0.910 g/cm$^3$. Resin of which the density is smaller than the lowermost limit is unfavorable, since its self-tackiness intrinsic to plastic resin will be high and its feel to the skin is not good.

The particles 13 may be of any type so far as they are not thermally deformed and are safe to human bodies. Among these, preferred are inorganic particles of at least one selected from the group consisting of titanium oxide, calcium carbonate, soda ash, gypsum, calcium sulfate, barium sulfate, sodium sulfate, magnesium carbonate, magnesium sulfate, clay, calcium phosphate, silicic anhydride, carbon and talc, as well as plastic beads of which the melting point is higher than that of the thermoplastic resin 11, as they are more effective for reducing the stickiness of the top sheet 1 in wet. More preferred is calcium carbonate.

Preferably, the particle size of the particles 13 falls between 2 $\mu$m and 20 $\mu$m. Particles having a larger particle size than the defined range will too much roughen the surface of the top sheet 1, and will give a hard feel to the skin, thereby detracting from the softness of the top sheet 1. In addition, such large particles will unevenly disperse in the thermoplastic resin 11 to further roughen the surface of the top sheet 1. On the other hand, particles having a smaller particle size than the defined range could not well roughen the surface of the top sheet 1, and could not reduce the contact area of the top sheet 1 to the skin to a desired degree, so that the top sheet 1 tends to have a sticky and stuffy feel. More preferably, the particle size of the particles 13 falls between 2 and 10 $\mu$m, even more preferably between 2 and 6 $\mu$m. The particle size referred to herein is meant to indicate the mean particle size of the particles.

Preferably, the outer resin layer 10 contains from 30 to 60 parts by weight, relative to 100 parts by weight of the thermoplastic resin 11 forming it, of the particles 13. If the content of the particles 13 is smaller than the defined range, the top sheet 1 will have a sticky and stuffy feel. On the other hand, if the content thereof is larger than the defined range, the resin for forming the outer resin layer 11 will be difficult to extrude out through an extruder and will lose the stability in film formation. If so, the strength of the top sheet 1 finally formed will be low.

While the absorbent article is used, its outer resin layer 10 is kept in direct contact with the skin of the wearer. Therefore, it is desirable that the surface roughness of the outer resin layer 10 is lower. Concretely, the surface roughness (MMD) of the outer resin layer 10 is at most 0.01. If its surface roughness is larger than the defined range, the outer resin layer 10 will have a rough feel. More preferably, its surface roughness is at most 0.005. To clarify the relationship between the surface roughness of the outer resin layer 10 and the content therein of the particles 13 with varying the particle size of the particles 13, the following experiment was carried out.

To prepare samples, 100 parts by weight of a thermoplastic resin, polyethylene (LLDPE, linear low-density polyethylene, having a density of 0.917 g/cm$^3$) was blended with a varying amount of particles (CaCO$_3$), with the particle size of the particles being varied as shown in Table 1. The samples were individually formed into films all having a thickness of 25 $\mu$m, and the surface roughness (MMD) of the films was measured by use of a texture feel tester, Katotec's KES with sensor terminals 5×5, under a load of 25 g. As a comparative sample, films not containing the particles were tested in the same manner as herein. The data obtained are given in Table 1.

TABLE 1

| Sample | 1 | 2 | 3 | 4 |
|---|---|---|---|---|
| Content of Particles | 30% | 40% | 50% | 60% |
| Size of Particles | | | | |
| 2.3 $\mu$m | 0.0050 | 0.0063 | 0.0062 | 0.0060 |
| 3.3 $\mu$m | 0.0069 | 0.0073 | 0.0088 | 0.0095 |
| 5.4 $\mu$m | 0.0076 | 0.0082 | 0.0096 | 0.0108 |

TABLE 1-continued

| Sample | 1 | 2 | 3 | 4 |
|---|---|---|---|---|
| 8 μm | 0.0102 | 0.0112 | 0.0120 | 0.0124 |
| 15 μm | 0.0118 | 0.0120 | 0.0145 | 0.0146 |
| Comparative Sample (with no particles) | 0.0060 | — | — | — |

The data in Table 1 indicate that the surface roughness of the films containing larger particles is larger, therefore confirming that larger particles in the films have a more significant influence on the surface roughness of the films containing them. In order that the films have a preferred surface roughness, the content of the particles having a particle size of at most 5.4 μm therein is preferably at most 50% or the content of the particles having a particle size of at most 3.3 μm therein is preferably at most 60%. More preferably, the content of the particles having a particle size of at most 2.3 μm in the films is at most 30%.

Preferably, the outer resin layer 10 has an LC value (load in compression) of at most 0.65, more preferably at most 0.55, in order that the absorbent article does not give a hard and rough feel to the wearer while it is rubbed and pressed against the skin of the wearer. To clarify the relationship between the LC value (load in compression) and an RC value (rate of recovery) of films containing a varying amount of particles 13, the following experiment was carried out.

Samples were prepared in the same manner as in the experiment for surface roughness. These samples contained calcium carbonate particles having a mean particle size of 5.4 μm. The varying content of the particles in these is given in Table 2. The samples were tested to measure the LC value (load in compression) and the RC value (rate of recovery) thereof. The data obtained are given in Table 2.

TABLE 2

| Sample | 5 | 6 | 7 | 8 |
|---|---|---|---|---|
| Content of particles | 0% | 30% | 40% | 50% |
| LC Value | 0.581 | 0.613 | 0.625 | 0.685 |
| RC Value | 47.0 | 43.3 | 35.3 | 35.6 |

The data indicate that the load in compression of the films increases and the bulk recovery thereof decreases with the increase in the content of the particles therein, therefore confirming that the films containing a larger amount of the particles are more tough and rigid but their durability is lower.

On the other hand, the thermoplastic resin for forming the inner resin layer 20 may be the same as that for forming the outer resin layer 10. However, it is desirable that the density of the thermoplastic resin for forming the inner resin layer 20 is lower than that of the thermoplastic resin for forming the outer resin layer 10. As containing the particles 13, the outer resin layer 10 has a tough and rigid feel in some degree. However, since the thermoplastic resin for forming the inner resin layer 20 has a low density, the top sheet 1 is soft and flexible as a whole. For its behavior, the top sheet 1 is elastic to compression without restraint, and is therefore not resistant to the movement of the skin of a wearer. Preferably, the resin density of the inner resin layer 20 is at most 0.905 g/cm$^3$. Also preferably, the inner resin layer 20 does not contain the particulate material which the outer resin layer 10 contains. In the absence of such a particulate material in the inner resin layer 20 therein, the top sheet 1 could be softer and more flexible. It should be noted that the inner resin layer 20 may contain such a particulate material so far as the particulate material content therein is smaller than that in the outer resin layer 10.

Specific examples of the thermoplastic resin for forming the inner resin layer 20 are VLDPE (very-low-density polyethylene) having a density of at most 0.900 g/cm$^3$; SEPS (manufactured by Kuraray Co., Ltd.—this is a hydrogenated block copolymer of polystyrene and polyisoprene, having a density of 0.89 g/cm$^3$); and amorphous or low-crystalline α-olefin copolymers, ethylene-α-olefin copolymers, and propylene-α-olefin copolymers (e.g., Toughmer manufactured by Mitsui Chemical Co., Ltd, having a density of 0.87 g/cm$^3$). Synthetic elastomer resins such as polyurethane and SEBS are also usable for the inner resin layer 20. However, since they are too much self-tacky, their films often adhere to each other (the film-to-film adhesion is referred to as blocking) while they are rolled up in their production, and the rolled films will be often damaged when unrolled. In this case, it is desirable to add a silicone-type release agent to the resins. Apart from these, a resin mixture prepared by blending a resin having a density of at least 0.900 g/cm$^3$ and a resin having a density of not larger than 0.900 g/cm$^3$ may be used for forming the inner resin layer 20.

The two-layered laminate resin film to be processed into the top sheet 1 may be prepared through co-extrusion of two resins for forming the outer resin layer 10 and the inner resin layer 20. If required, an adhesive layer may be interposed between the outer resin layer and the inner resin layer.

Preferably, the top sheet 1 has a thickness falling between about 20 and 35 μm or so, in view of its strength and flexibility and the shape retaining ability of the perforations 4 formed through it. To reduce the sticky feel of the top sheet 1, the thickness of the outer resin layer 10 preferably falls between 15 and 60% of the overall thickness of the top sheet 1. Furthermore, to ensure the flexibility of the top sheet 1, the thickness of the inner resin layer 20 preferably falls between 40 and 85% of the overall thickness of the top sheet 1.

The top sheet 1 has a large number of perforations 4 formed in its overall area through it. As shown in FIG. 2, the perforations 4 all protrude from the surface is of the top sheet 1 into the inside of the absorbent article, or that is, into the absorbent layer 2, with their inner diameter decreasing in the direction toward the absorbent layer 2. One advantage of the perforations 4 formed in that manner is that the excretions first received by the top sheet 1 can easily move from the surface of the top sheet 1 to the absorbent layer 2 owing to the capillary action of the perforations 4, and that the excretions thus absorbed by the absorbent layer 2 are hardly returned back to the top sheet 1. Another advantage thereof is that the perforations 4 increase the apparent thickness of the top sheet 1 and therefore can keep the excretions having been absorbed by the absorbent layer 2 away from the skin of the wearer. With that, the wearer could be free from the unpleasant feel of the wetted absorbent article.

One method for forming the perforations 4 through the top sheet 1 comprises, for example, setting a laminate film of the outer resin layer 10 and the inner resin layer 20 on a perforating drum, and vacuumizing it under suction through holes provided with the perforating drum with hot air being applied thereto whereby the intended perforations 4 that correspond to the holes of the perforating drum are formed in the overall area of the laminate film through it. In this method, an inner wall of each perforation 4 is formed of the outer resin layer 10, as shown in FIG. 2. In the top sheet 1 thus produced, the perforations 4 are so constituted that the tough outer resin layer 10 forms the inner walls thereof and the soft and flexible inner resin layer 20 underlies the outer resin layer 10. Accordingly, the perforations 4 well keep their shape, and they can be readily restored to their original condition, even if deformed while the absorbent article is used.

Regarding the configuration of the perforations 4 to ensure easy permeation of excretions through them and to ensure their shape retaining ability, it is desirable that the inner diameter 4R of each perforation 4 in the surface 1s of the top sheet 1 falls between 0.6 and 1.5 mm or so, that the inner diameter 4r thereof on the side of the absorbent layer 2 falls between 0.3 and 1.3 mm or so, that the depth 4h thereof from the surface 1s (this corresponds to the apparent thickness of the top sheet 1) falls between 0.3 and 0.6 mm or so, that the distance 4s between the neighboring perforations 4 in the surface 1s falls between 0.05 and 0.2 mm or so, and that the distance 4t between the neighboring perforations 4 on the side of the absorbent layer 2 falls between 0.2 and 0.4 mm or so. Also preferably, the overall area of the perforations 4 falls between 60 and 80% of the overall area of the top sheet 1.

Preferably, the top sheet 1 contains fine particles of dye having a mean particle size of about 0.2 $\mu$m or so, apart from the particles 13, in which the additional dye particles act to mask the excretions absorbed by the absorbent article. For example, such fine particles may be added to the films to be the outer resin layer 10 and/or the inner resin layer 20 while the films are formed. Preferably, the amount of the fine particles to be added thereto falls between 2 and 5 parts by weight or so relative to 100 parts by weight of the thermoplastic resin to form the films. In general, fine particles of titanium oxide are used for increasing the degree of whiteness of the top sheet 1.

To promote the permeation of excretions thereinto, the top sheet 1 may be coated with a hydrophilic surfactant.

In the absorbent article of the invention, for example, the absorbent layer 2 may be a liquid pervious fibrous layer of beaten pulp optionally combined with SAP (super absorbent polymer). Preferably, the absorbent layer 2 is wrapped with a liquid pervious sheet such as tissue paper or the like. As the case may be, sheets of water-absorbing paper may be stacked to form the absorbent layer 2.

The back sheet 3 disposed on the back surface of the absorbent layer 2 may be an air-pervious but liquid impervious polyolefin resin film or the like. Around the absorbent layer 2, the top sheet 1 and the back sheet 3 are bonded to each other with a hot-melt adhesive or the like. Preferably, the top sheet 1 is partly bonded to the adsorbent layer 2 with a hot-melt adhesive. In this case, excretions can be easily led to the absorbent layer 2, thereby hardly staying in the top sheet 1.

If desired, a non-woven fabric sheet of hydrophilicated thermoplastic synthetic fibers prepared in a mode of, for example, air-through processing, point bonding or spun lace working may be bonded to the outer surface of the top sheet 1 with a hot-melt adhesive to give a composite top sheet. The composite top sheet may be partly bonded to the absorbent layer 2. Without lowering its liquid perviousness therethrough, this composite type top sheet can keep absorbed excretions more away from the skin of the wearer. Especially, preferred is a non-woven fabric prepared in a mode of air-through processing, as it is bulky and can act as a cushion.

If desired, such a non-woven fabric may be bonded to the top sheet 1 through heat embossing to give a composite top sheet, and the composite top sheet may be bonded to an absorbent core. Heat embossing is preferred rather than bonding with a hot-melt adhesive, since the composite top sheet produced can have a higher wet strength and, in addition, the non-woven fabric is prevented from being peeled off from the top sheet 1. The heat-embossing pattern is not specifically defined, including, for example, dot patterns, screen-like patterns, etc. However, it is desirable that the embossed pattern area falls between 3 and 20% of the overall area of the composite top sheet for ensuring good wet strength without lowering the liquid perviousness of the sheet.

EXAMPLES

The invention is described in more detail with reference to the following Examples, which, however, are not intended to restrict the scope of the invention.

A top sheet 1 as shown in FIGS. 1 and 2 was produced for the absorbent article of the invention. Precisely, a low-density polyethylene resin (LLDPE) having a density of 0.917 g/cm$^3$ was blended with 50 parts by weight of calcium carbonate particles having a mean particle size of 5.4 $\mu$m to prepare a resin component for the outer resin layer 10; and a low-crystalline ethylene-α-olefin copolymer having a density of 0.89 g/cm$^3$ was prepared for the inner resin layer 20. The two resin layers were co-extruded to form a two-layered laminate resin film, in which the thickness of the outer resin layer 10 was 10 $\mu$m and that of the inner resin layer 20 was 15 $\mu$m.

The thus-formed laminate resin film was set on a perforating plastic sheet. It should be noted that the perforating plastic sheet was employed in the shown example in place of the perforating drum described above. Next, the laminate resin film was vacuumized under suction through holes provided in the plastic sheet with hot air at 280 to 320° C. being applied thereto whereby the intended perforations 4 corresponding to the holes of the perforating drum were formed in the overall area of the laminate resin film through it. The perforation pattern of the plastic sheet used herein corresponds to that of the top sheet 1 illustrated in FIG. 1. As in FIG. 3 showing the cross section of the plastic sheet 30 used herein, the distance 31 between the neighboring holes 40 in the upper surface of the plastic sheet 30 falls between 0.05 and 0.14 mm or so; the diameter 32 of each hole 40 falls between 0.5 and 1.6 mm or so; the distance 33 between the neighboring holes 40 in the lower surface of the plastic sheet 30 falls between 0.3 and 0.35 mm or so; the distance 34 between the neighboring holes 40 in the middle of the upper surface and the lower surface of the plastic sheet 30 falls between 0.15 and 0.3 mm; and the thickness 35 of the plastic sheet 30 falls between 0.3 and 0.6 mm or so. The top sheet thus produced was tested to measure its LC value (load in compression) and RC value (rate of recovery), and to measure the load for its varying elongation as shown in Table 3. The data thus obtained are given in Table 3. For comparison, the materials for the outer resin layer and the inner resin layer were mixed and formed into a film, and the film was perforated in the same manner as herein. This was tested also in the same manner as herein, and its data are given in Table 3.

TABLE 3

|  | Comparative Example | Example |
|---|---|---|
| Content of Particles | 0% | 50% |
| LC Value | 0.554 | 0.501 |
| RC Value | 47.0 | 54.9 |
| Load for 3% Elongation | 45 | 19 |
| Load for 5% Elongation | 82 | 34 |
| Load for 10% Elongation | 168 | 79 |

From the data as above, it is understood that the LC value of the top sheet for the absorbent article of the invention is decreased and the RC value thereof is increased. In addition, it is also understood that, since the load for its elongation is low, the top sheet does not give a tough feel to the skin rubbed against it.

As set forth above, the top sheet of the absorbent article of the invention has a little plastic-like sticky and stuffy feel, though it is made of resin. Therefore, wearers could be free from an unpleasant feel while using the absorbent article of the invention. In addition, though the top sheet contains the particulate material, it is soft and flexible and is movable relatively freely. Further, the top sheet is well elastic to compression, and does not resist to the movement of the skin of wearers.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. An absorbent article comprising:

an absorbent layer; and a top sheet having a number of perforations and disposed on a body facing surface of the absorbent layer, the top sheet being made of a multi-layered resin film having at least two resin layers consisting of an outer resin layer located at a distal side of the top sheet relative to the body facing surface and at least one inner resin layer located at a proximal side of the top sheet relative to the body facing surface of the absorbent layer, at least the outer resin layer containing a particulate material having a mean particle size of from 2 $\mu$m to 20 $\mu$m for attaining a predetermined stiffness necessary for ensuring a comfortable fit, and the inner resin layer having the resin density smaller than that of the outer resin layer for attaining a level of flexibility necessary for providing flexibility for the top sheet.

2. The absorbent article as set forth in claim 1, wherein the inner resin layer does not contain the particulate material.

3. The absorbent article as set forth in claim 1, wherein at least a part of the particulate material is exposed outside the outer resin layer.

4. The absorbent article as set forth in claim 1, wherein the resin density of the outer resin layer is at least 0.91 g/cm$^3$.

5. The absorbent article as set forth in claim 1, wherein the resin density of the inner resin layer is at most 0.90 g/cm$^3$.

6. The absorbent article as set forth in claim 1, wherein the outer resin layer contains from 30 to 60 parts by weight, relative to 100 parts by weight of the resin that forms the outer resin layer, of the particulate material.

7. The absorbent article as set forth in claim 1, rein the thickness of the outer resin layer is from 15 to 60%, and the thickness of the inner resin layer is from 40 to 85%, relative to 100% of the thickness of the multi-layered in film.

8. The absorbent article as set forth in claim 1, wherein each perforation has an inner wall protruding from an inner surface of the top sheet toward the absorbent layer.

9. The absorbent article as set forth in claim 1, wherein the top sheet made of the multi-layered resin film is partly bonded to the absorbent layer.

10. The absorbent article as set forth in claim 1, wherein a water-impervious non-woven fabric is bonded to the inner surface of the top sheet made of the multi-layered resin film to form a combined sheet, and the combined sheet is partly bonded to the absorbent layer.

11. An absorbent article comprising:

an absorbent layer; and a top sheet having a number of perforations and disposed on a body facing surface of said absorbent layer, said top sheet being made of a multi-layered resin film having at least two resin layers consisting of an outer resin layer made of thermoplastic resin and located at a distal side of said top sheet relative to said body facing surface and at least one inner resin layer made of a thermoplastic resin that identical to said outer resin layer and located at a proximal side of said top sheet relative to said body facing surface of said absorbent layer, at least said outer resin layer containing a particulate material having a mean particle size of from 2 $\mu$m to 20 $\mu$m for attaining a predetermined stiffness necessary for ensuring a comfortable fit, and said inner resin layer having a resin density which is smaller than that of said outer resin layer for attaining a level of flexibility necessary for providing flexibility for said top sheet.

12. An absorbent article comprising:

an absorbent layer; and a top sheet having a number of perforations and disposed on a body facing surface of said absorbent layer, said top sheet being made of a multi-layered resin film having at least two resin layers consisting an outer resin layer located at a distal side of said top sheet relative to said body facing surface and at least one inner resin layer located at a proximal side of said top sheet relative to said body facing surface of said absorbent layer, at least said outer resin layer containing a particulate material having a mean particle size of from 2 $\mu$m to 20 $\mu$m for attaining a predetermined stiffness necessary for ensuring a comfortable fit, said outer resin layer containing from 30 to 60 parts by weight, relative to 100 parts by weight of a resin that forms said outer resin layer, of the particulate material, and said inner resin layer having a resin density which is smaller than that of the outer resin layer for attaining a level of flexibility necessary for providing flexibility for said top sheet.

* * * * *